US007329228B2

(12) United States Patent
Burbank et al.

(10) Patent No.: US 7,329,228 B2
(45) Date of Patent: *Feb. 12, 2008

(54) METHODS AND APPARATUS FOR SECURING MEDICAL INSTRUMENTS TO DESIRED LOCATIONS IN A PATIENT'S BODY

(75) Inventors: Fred H. Burbank, San Juan Capistrano, CA (US); Paul Lubock, Laguna Niguel, CA (US); Michael L. Jones, Capistrano Beach, CA (US); Richard L. Quick, Trabuco Canyon, CA (US)

(73) Assignee: SenoRx, Inc.

( * ) Notice: Subject to any disclaimer, the term of this patent is extended or adjusted under 35 U.S.C. 154(b) by 0 days.

This patent is subject to a terminal disclaimer.

(21) Appl. No.: 11/179,277

(22) Filed: Jul. 11, 2005

(65) Prior Publication Data

US 2005/0245842 A1 Nov. 3, 2005

Related U.S. Application Data

(63) Continuation of application No. 10/010,213, filed on Dec. 4, 2001, now Pat. No. 7,264,596, which is a continuation of application No. 09/146,185, filed on Sep. 1, 1998, now Pat. No. 6,540,693, which is a continuation-in-part of application No. 09/057,303, filed on Apr. 8, 1998, now Pat. No. 6,331,166.

(60) Provisional application No. 60/076,973, filed on Mar. 3, 1998.

(51) Int. Cl.
*A61B 10/00* (2006.01)
*A61B 17/32* (2006.01)

(52) U.S. Cl. .................. 600/567; 600/563; 600/564

(58) Field of Classification Search ............... 600/564, 600/565, 566, 567, 568; 604/171; 606/167, 606/170, 174
See application file for complete search history.

(56) References Cited

U.S. PATENT DOCUMENTS 2,032,860 A 3/1936 Wappler et al.

(Continued)

FOREIGN PATENT DOCUMENTS

DE 19528440 A 8/1995

(Continued)

OTHER PUBLICATIONS

J. S. Armstrong et al. "Differential marking of excision planes in screened breast lesions by organically coloured gelantins [see comments]" Journal of Clinical Pathology (Jul. 1990) 43(7):604-7, XP000-971447 abstract; tables 1 and 2.

(Continued)

*Primary Examiner*—Max F. Hindenburg
*Assistant Examiner*—Jonathan Foreman
(74) *Attorney, Agent, or Firm*—Edward J. Lynch

(57) ABSTRACT

Devices and methods are provided for securely affixing a medical instrument to desired tissue in a patient's body, using a fixation agent. Such medical instruments may comprise localization wires or tissue acquisition instruments, such as biopsy instruments, for example. In the case of tissue acquisition instruments, the inventors have discovered significant advantages for securely affixing the distal end of the tissue acquisition instrument to a particular tissue target area. For example, such an approach permits the imaging environment to be uncoupled from the procedural environment so that expensive and often unavailable imaging equipment, such as stereotactic imaging equipment, need not be used. In a preferred embodiment, a bonding agent, such as adhesive, surgical glue, or a solvent, is used as the fixation agent.

14 Claims, 12 Drawing Sheets

U.S. PATENT DOCUMENTS

| | | | |
|---|---|---|---|
| 3,805,791 A | 4/1974 | Seuberth et al. | |
| 3,955,578 A | 5/1976 | Chamness et al. | |
| 4,007,732 A | 2/1977 | Kvavle et al. | |
| 4,202,338 A | 5/1980 | Bitrolf | |
| 4,294,254 A | 10/1981 | Chamness | |
| 4,311,143 A | 1/1982 | Komiya | |
| 4,362,160 A | 12/1982 | Hiltebrandt | |
| 4,425,908 A | 1/1984 | Simon | |
| 4,503,855 A | 3/1985 | Maslanka | |
| 4,576,162 A | 3/1986 | McCorkle | |
| 4,592,356 A | 6/1986 | Gutierrez | |
| 4,616,656 A | 10/1986 | Nicholson et al. | |
| 4,638,802 A | 1/1987 | Okada | |
| 4,682,606 A | 7/1987 | DeCaprio | |
| 4,718,419 A | 1/1988 | Okada | |
| 4,724,836 A | 2/1988 | Okada | |
| 4,774,948 A | 10/1988 | Markham | |
| 4,966,583 A | 10/1990 | Debbas | |
| 5,007,908 A | 4/1991 | Rydell | |
| 5,024,617 A | 6/1991 | Karpiel | |
| 5,035,696 A | 7/1991 | Rydell | |
| 5,047,027 A | 9/1991 | Rydell | |
| 5,059,197 A | 10/1991 | Urie et al. | |
| 5,064,424 A | 11/1991 | Bitrolf | |
| 5,066,295 A | 11/1991 | Kozak et al. | |
| 5,078,716 A | 1/1992 | Doll | |
| 5,080,660 A | 1/1992 | Buelna | |
| RE33,925 E | 5/1992 | Bales et al. | |
| 5,111,828 A | 5/1992 | Kornberg et al. | |
| 5,133,359 A | 7/1992 | Kedem | |
| RE34,056 E | 9/1992 | Lindgren et al. | |
| 5,158,084 A | 10/1992 | Ghiatas | |
| 5,158,561 A | 10/1992 | Rydell et al. | |
| 5,163,938 A | 11/1992 | Kambara et al. | |
| 5,196,007 A | 3/1993 | Ellman et al. | |
| 5,201,732 A | 4/1993 | Parins et al. | |
| 5,201,741 A | 4/1993 | Dulebohn | |
| 5,207,686 A | 5/1993 | Dolgin | |
| 5,217,458 A | 6/1993 | Parins | |
| 5,221,269 A | 6/1993 | Miller et al. | |
| 5,224,488 A | 7/1993 | Neuffer | |
| 5,234,426 A | 8/1993 | Rank et al. | |
| 5,312,400 A | 5/1994 | Bales et al. | |
| 5,318,564 A | 6/1994 | Eggers | |
| 5,323,768 A | 6/1994 | Saito et al. | |
| 5,324,288 A | 6/1994 | Billings et al. | |
| 5,335,671 A | 8/1994 | Clement | |
| 5,344,420 A | 9/1994 | Hilal et al. | |
| 5,353,804 A | 10/1994 | Kornberg et al. | |
| 5,376,094 A | 12/1994 | Kline | |
| 5,380,321 A | 1/1995 | Yoon | |
| 5,395,312 A | 3/1995 | Desai | |
| 5,409,004 A | 4/1995 | Sloan | |
| 5,415,656 A | 5/1995 | Tihon et al. | |
| 5,417,687 A | 5/1995 | Nardella et al. | |
| 5,417,697 A | 5/1995 | Wilk et al. | |
| 5,423,770 A | 6/1995 | Yoon | |
| 5,423,814 A | 6/1995 | Zhu et al. | |
| 5,437,665 A | 8/1995 | Munro | |
| 5,441,503 A | 8/1995 | Considine et al. | |
| 5,449,382 A | 9/1995 | Dayton | |
| 5,462,553 A | 10/1995 | Dolgin | |
| 5,477,862 A | 12/1995 | Haga | |
| 5,484,436 A | 1/1996 | Eggers et al. | |
| 5,488,958 A | 2/1996 | Topel et al. | |
| 5,501,654 A | 3/1996 | Failla et al. | |
| 5,526,822 A | 6/1996 | Burbank et al. | |
| 5,527,331 A | 6/1996 | Kresch et al. | |
| 5,542,948 A | 8/1996 | Weavers et al. | |
| 5,562,102 A | 10/1996 | Taylor | |
| 5,611,803 A | 3/1997 | Heaven et al. | |
| 5,643,282 A | 7/1997 | Kieturakis | |
| 5,649,547 A | 7/1997 | Ritchart et al. | |
| 5,653,718 A | 8/1997 | Yoon | |
| 5,665,085 A | 9/1997 | Nardella | |
| 5,674,184 A | 10/1997 | Hassler, Jr. | |
| 5,683,384 A | 11/1997 | Gough et al. | |
| 5,697,946 A * | 12/1997 | Hopper et al. | 606/185 |
| 5,700,273 A | 12/1997 | Buelna et al. | |
| 5,735,847 A | 4/1998 | Gough et al. | |
| 5,749,887 A | 5/1998 | Heske et al. | |
| 5,752,972 A | 5/1998 | Hoogeboom | |
| 5,755,697 A | 5/1998 | Jones et al. | |
| 5,766,163 A | 6/1998 | Mueller et al. | |
| 5,769,086 A | 6/1998 | Ritchart et al. | |
| 5,794,626 A | 8/1998 | Kieturakis | |
| 5,795,308 A | 8/1998 | Russin | |
| 5,800,445 A | 9/1998 | Ratcliff et al. | |
| 5,810,764 A | 9/1998 | Eggers et al. | |
| 5,810,806 A | 9/1998 | Ritchart et al. | |
| 5,823,971 A * | 10/1998 | Robinson et al. | 600/567 |
| 5,840,044 A * | 11/1998 | Dassa et al. | 600/567 |
| 5,868,740 A | 2/1999 | LeVeen et al. | |
| 5,879,357 A | 3/1999 | Heaton et al. | |
| 5,947,964 A | 9/1999 | Eggers et al. | |
| 5,954,670 A | 9/1999 | Baker | |
| 6,022,362 A | 2/2000 | Lee et al. | |
| 6,059,734 A | 5/2000 | Yoon | |
| 6,117,153 A * | 9/2000 | Lary et al. | 606/170 |
| 6,280,450 B1 | 8/2001 | McGuckin, Jr. | |
| 6,312,429 B1 | 11/2001 | Burbank et al. | |
| 6,363,940 B1 | 4/2002 | Krag | |
| 6,454,727 B1 | 9/2002 | Burbank et al. | |
| 6,494,881 B1 | 12/2002 | Bales et al. | |
| 6,540,695 B1 | 4/2003 | Burbank et al. | |
| 6,638,234 B2 | 10/2003 | Burbank et al. | |
| 6,679,851 B2 | 1/2004 | Burbank et al. | |
| 6,712,775 B2 | 3/2004 | Burbank et al. | |
| 6,716,179 B2 | 4/2004 | Burbank et al. | |
| 2002/0068879 A1 | 6/2002 | Lubock et al. | |
| 2002/0077628 A1 | 6/2002 | Burbank et al. | |
| 2003/0144605 A1 | 7/2003 | Burbank et al. | |

FOREIGN PATENT DOCUMENTS

| | | |
|---|---|---|
| EP | 0472368 A | 8/1991 |
| EP | 0 601 709 A2 | 6/1994 |
| EP | 0 797 957 | 1/1997 |
| EP | 0 769 281 | 4/1997 |
| GB | 2311468 A | 2/1997 |
| WO | 98 08441 | 3/1990 |
| WO | GB94/01536 | 7/1994 |
| WO | GB 94/01537 | 7/1994 |
| WO | 94 27670 | 12/1994 |
| WO | 95/02370 | 1/1995 |
| WO | 95/02371 | 1/1995 |
| WO | 95 03843 | 2/1995 |
| WO | 95 10317 | 4/1995 |
| WO | 97/29702 | 8/1997 |
| WO | 98 24372 | 6/1998 |

OTHER PUBLICATIONS

Blackwell Science Ltd. "The Loop Electrode: New Device for US-Guided Interstitial Tissue Ablation Using Radio Frequency Electrosurgery—An Animal Study" 1996 *Min Incas Ther & Allied Technol* 5: 511-516.

International Search Report from PCT/US99/04471, mailed Jun. 14, 1999.

* cited by examiner

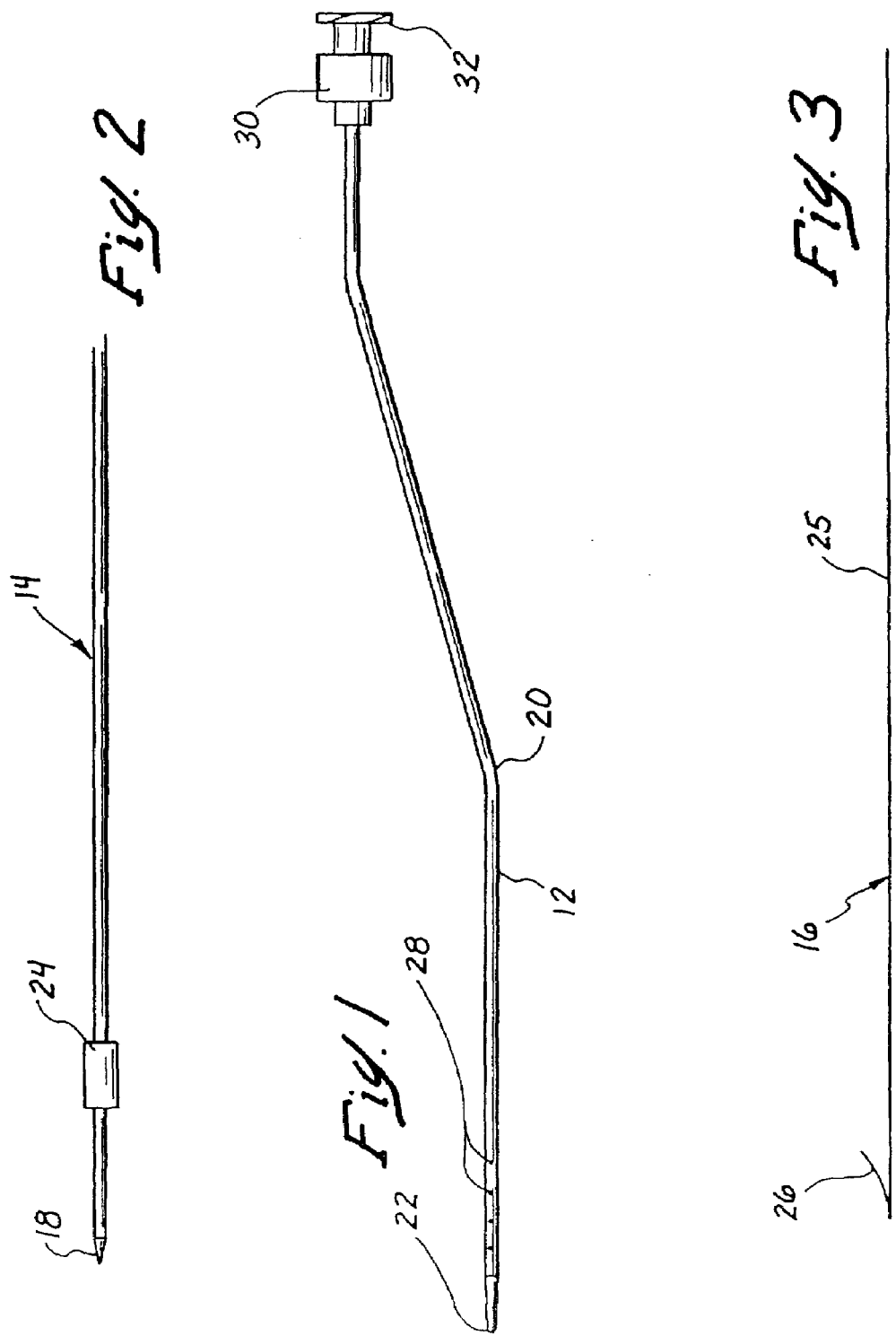

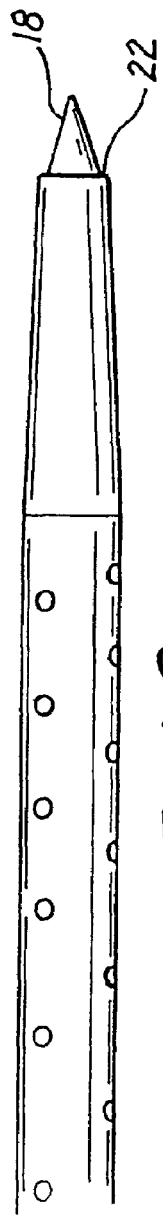
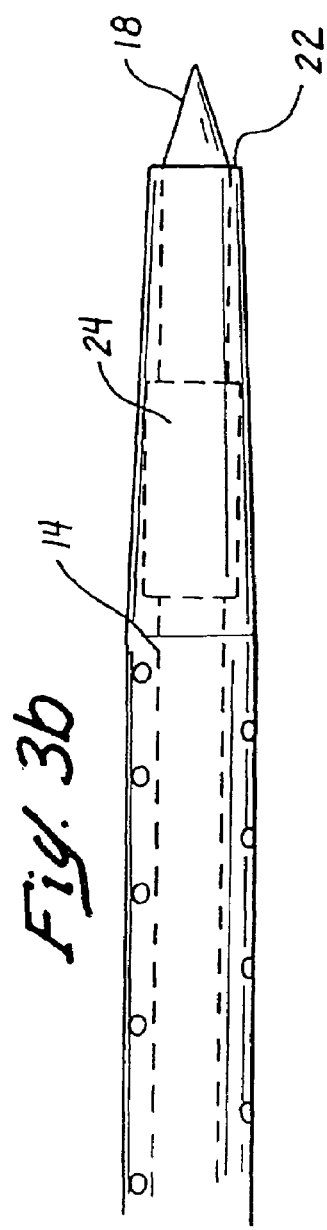
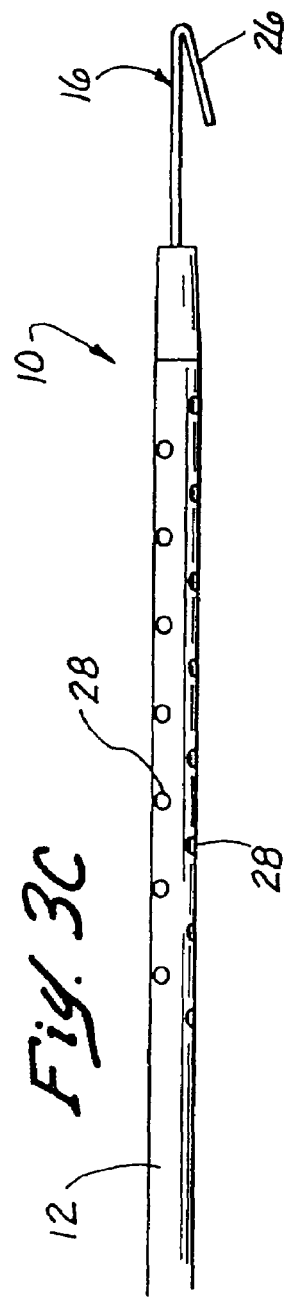
Fig. 3a
Fig. 3b
Fig. 3c

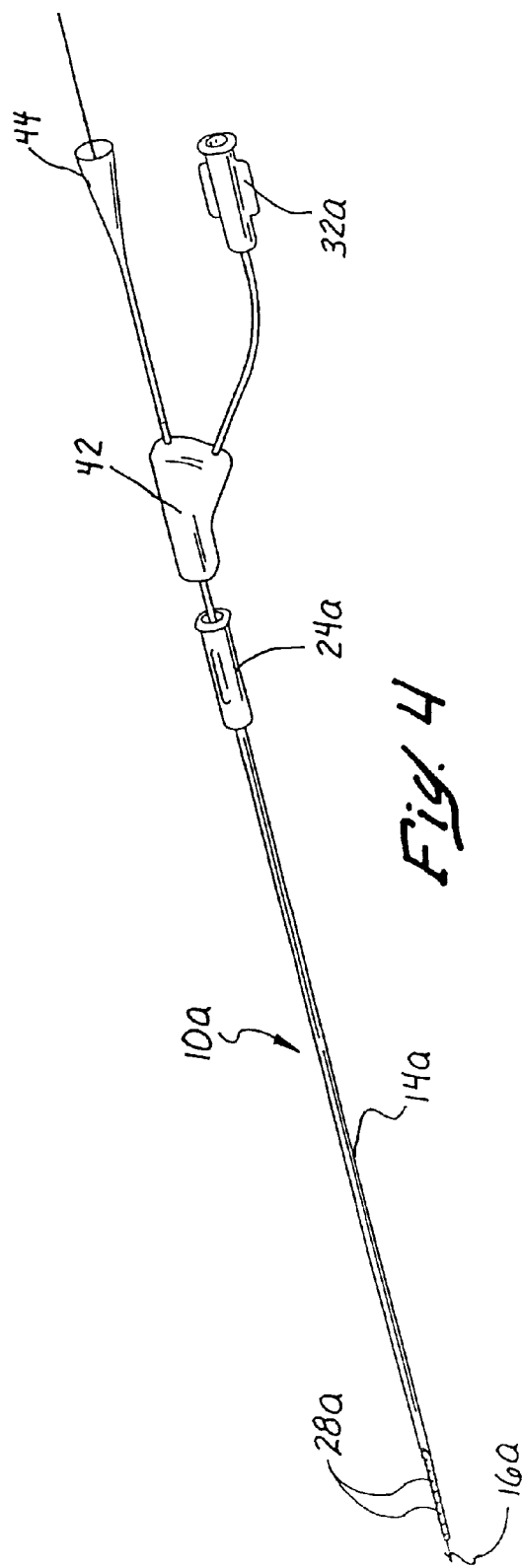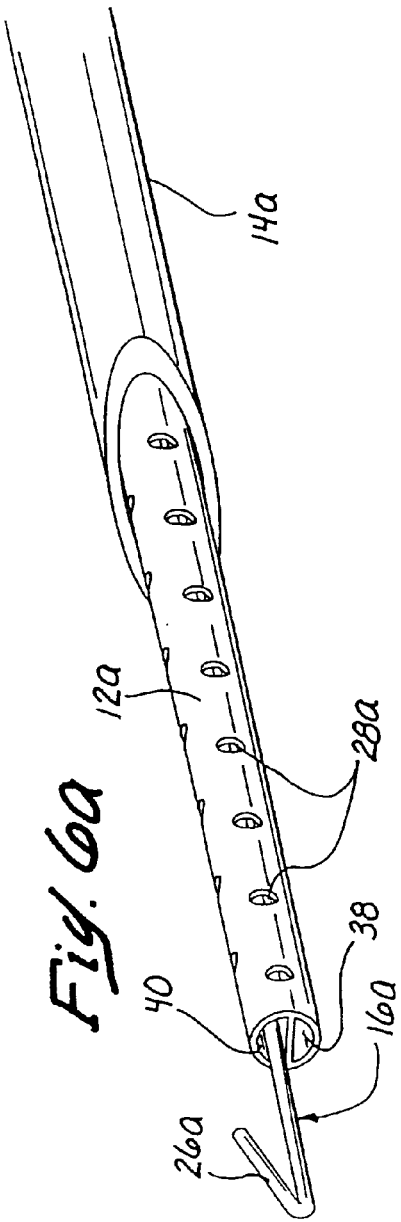

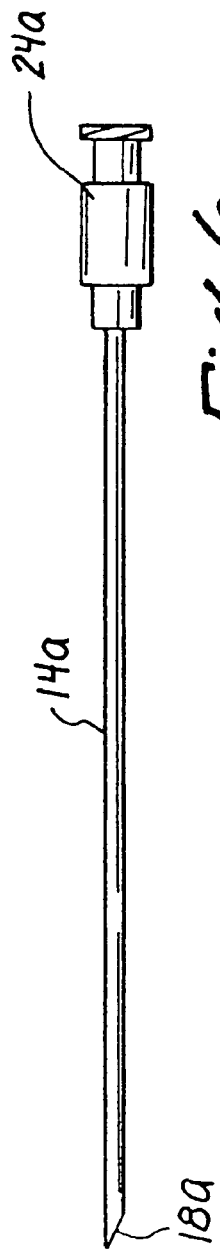
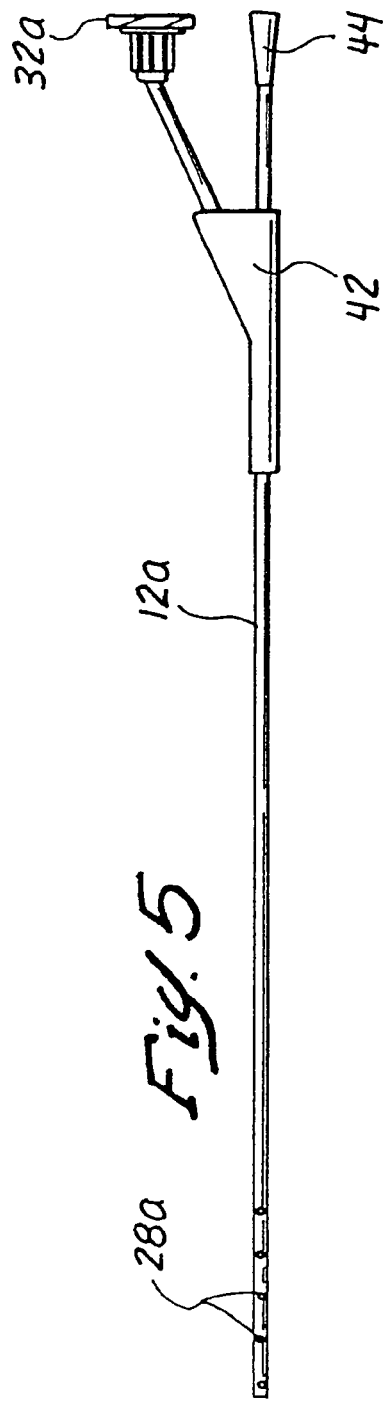
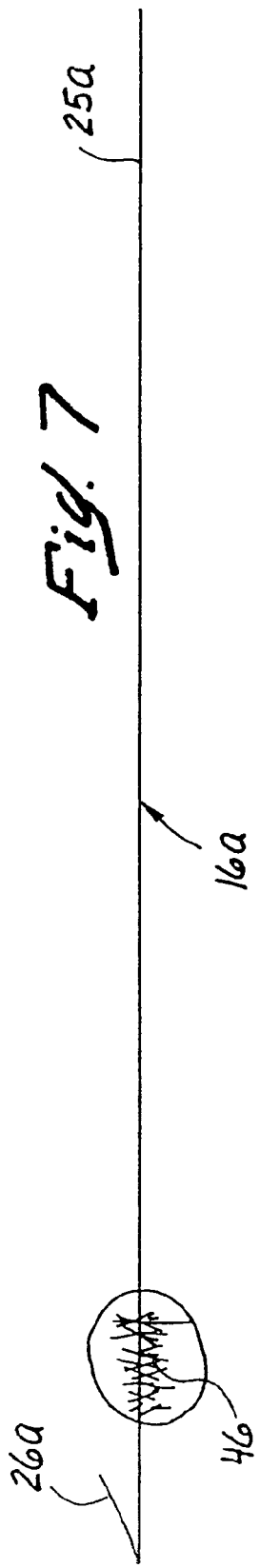

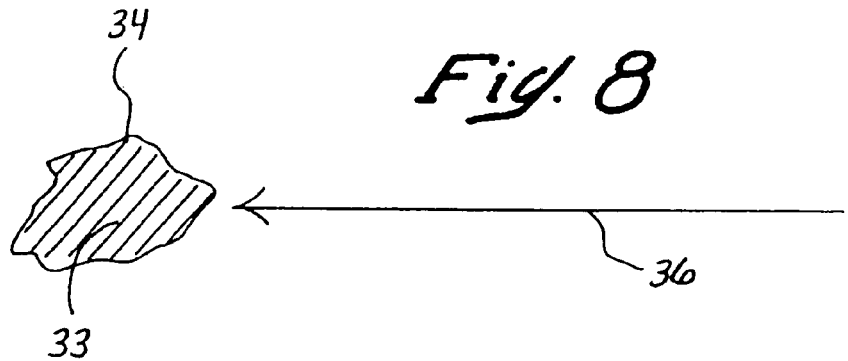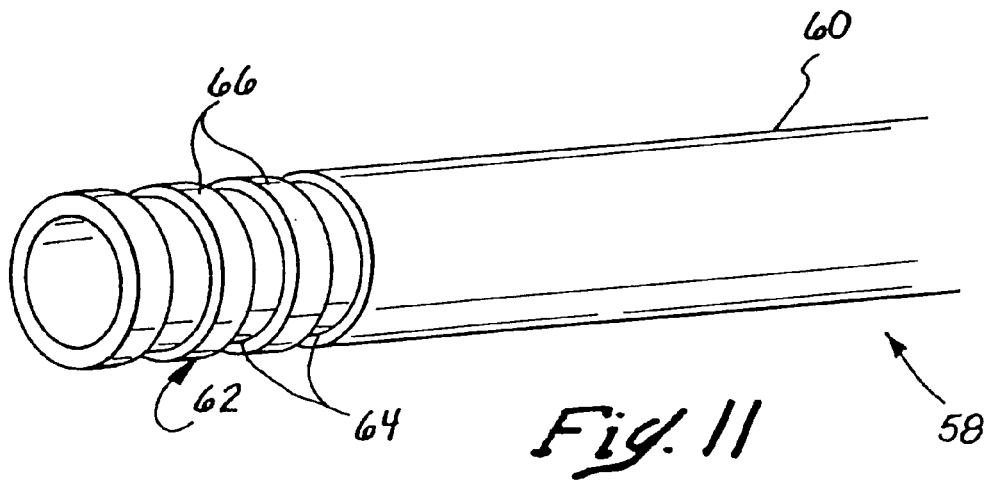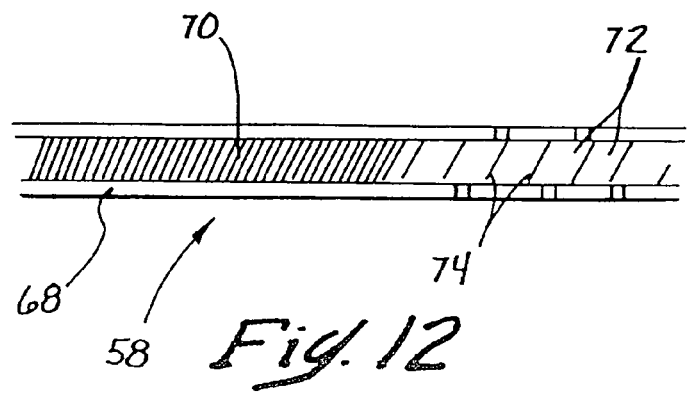

METHODS AND APPARATUS FOR SECURING MEDICAL INSTRUMENTS TO DESIRED LOCATIONS IN A PATIENT'S BODY

RELATED APPLICATIONS

This is a continuation application of application Ser. No. 10/010,213, filed Dec. 4, 2001 now U.S. Pat. No. 7,264,596, which is a continuation of Ser. No. 09/146,185, filed Sep. 1, 1998, now U.S. Pat. No. 6,540,693, which is a continuation-in-part of patent application Ser. No. 09/057,303, filed Apr. 8, 1998, now U.S. Pat. No. 6,331,166, which claims benefit to provisional patent application Ser. No. 60/076,973, filed Mar. 3, 1998, all of which applications are hereby incorporated herein by reference in their entirety and from which priority is hereby claimed under 35 U.S.C. §§119(e) and 120.

FIELD OF THE INVENTION

The present invention relates to methods and devices for ensuring that a medical instrument remains in a desired location within a patient's body during a medical procedure, and more particularly to methods and devices for affixing a distal end of the medical instrument to the desired location using adhesives.

BACKGROUND OF THE INVENTION

It is often desirable and frequently necessary to sample or remove a portion of tissue from humans and other animals, particularly in the diagnosis and treatment of patients with cancerous tumors. pre-malignant conditions, and other diseases or disorders.

Typically, in the case of cancer, particularly cancer of the breast, there is a great emphasis on early detection and diagnosis through the use of screening modalities, such as physical examination, and particularly mammography, which is capable of detecting very small-abnormalities, often nonpalpable. When the physician establishes by means of a mammogram or other screening modality, such as ultrasound, that suspicious circumstances exist, a biopsy must be performed to capture tissue for a definitive diagnosis as to whether the suspicious lesion is cancerous. Biopsy may be done by an open or percutaneous technique. Open biopsy is a surgical procedure using a scalpel and involving direct vision of the target area, for removing the entire mass (excisional biopsy) or a part of the mass (incisionial biopsy). Percutaneous biopsy, on the other hand, is usually done with a needle-like instrument through a relatively small incision, blindly or with the aid of an artificial imaging device, and may be either a fine needle aspiration (FNA) or a core biopsy. In FNA biopsy, individual cells or clusters of cells are obtained for cytologic examination and may be prepared such as in a Papanicolaou smear. In core biopsy, as the term suggests, a core or fragment of tissue is obtained for histologic examination which may be done via a frozen section or paraffin section.

The type of biopsy utilized depends in large part on circumstances present with respect to the patient, including the location of the lesion(s) within the body, and no single procedure is ideal for all cases. However, core biopsy is extremely useful in a number of conditions and is being used more frequently by the medical profession.

When an open surgical biopsy procedure is indicated, current practice dictates the use of lesion localization needles and devices, commonly referred to as "localization wires", for use in localizing or marking non-palpable lesions and tumors within the body. These devices generally comprise a hypodermic needle or cannula which is inserted into the body under local anesthesia to the lesion or tissue of interest. The wire marker, or localization wire, is then passed through the cannula and extends through the lesion of interest so that the distal end thereof is anchored beyond the lesion. Thus, the lesion is marked for subsequent surgical procedures such as excision or biopsy. The anchoring procedure is typically accomplished by means of mechanical structure disposed at the distal end of the wire marker, such as a barb, hook, or the like, which is attached to surrounding tissue. After marking the lesion with the wire marker, the cannula is usually removed from the body, leaving the wire in place and extending from the body, for subsequent use by the surgeon during the biopsy procedure in identifying the lesion location. However, it often occurs that the barb or hook at the distal end of the wire marker attaches to something other than the tumor or lesion. For example, in the case of breast biopsies, the breast will typically be placed in compression during the imaging procedure in order to properly identify the location of the target lesion and place the localization wire. However, breast tissue is comprised of fibrous bands which, in compression, may be close to the target lesion and inadvertently engaged by the barb of the localization wire. Later, when the breast is released from compression prior to the surgical procedure, the fibrous bands will move away from the target lesion, and the distal end of the localization wire may thus move a substantial distance away from the target lesion.

It would be desirable, therefore, to develop a localization wire system and method wherein the distal end of the localization wire could be positively attached to the target lesion in order to minimize the possibility of migration of the distal end of the localization wire away from the target lesion between the imaging and surgical procedures.

In circumstances where a core biopsy procedure is indicated, various systems are available. Such systems are shown, for example, in U.S. Pat. No. 5,526,822 to Burbank et al, which discloses a probe having a laterally disposed tissue receiving port at the distal end thereof for acquiring relatively small tissue samples, and in U.S. Pat. No. 5,111,828 to Kornberg et al., which discloses a probe having an axially disposed tissue receiving port at the distal end thereof for acquiring relatively large intact tissue samples. Both of these patents are expressly incorporated by reference herein.

U.S. application Ser. No. 09/057,303 to Burbank et al., commonly assigned with the present application and expressly incorporated by reference herein, discloses still another core biopsy apparatus, which advantageously permits the acquisition of tissue samples which are larger in diameter than the diameter of the instrument lumen, thereby greatly increasing the chances of completely removing the target lesion and leaving "clean" margins thereabout.

As in the case of localization wires, there is some risk in using any of the foregoing devices that the distal end of the instrument will migrate away from the target lesion during the biopsy procedure, thereby reducing the likelihood of removing target tissue. Heretofore, in the case of core biopsy procedures, the risk of this occurrence is minimized by employing image guidance techniques during the entire tissue removal procedure. For example, in the case of the '822 Burbank et al. patent, a stereotactic imaging guidance system is typically utilized during the disclosed procedure. One disadvantage of this approach, however, is that the patient's breast must remain in compression during the entire procedure, with attendant discomfort and increased procedural difficulty, in order to properly utilize the imaging equipment. Furthermore, stereotactic imaging equipment or other suitable alternatives can cost as much as $400,000 or more and is not in the usual inventory of a typical community hospital. It would therefore be quite advantageous if a method and apparatus could be developed which would permit the uncoupling of the imaging environment from the procedural environment without undue risk that the active or cutting end of the core biopsy instrument would migrate away from the target lesion during the interval between the imaging procedure and the biopsy procedure.

SUMMARY OF THE INVENTION

The present invention solves the problems outlined above by describing devices and methods for securely affixing a localization wire to desired tissue in a patient's body, so that after the patient is moved from the imaging environment to the procedural environment, the practitioner will have assurance that the localization wire is still accurately placed. Additionally, devices and methods are described for ensuring that the distal end of a tissue acquisition instrument, such as a biopsy instrument, is securely affixed to a particular target area, such as a lesion, in a patient's body, thereby advantageously permitting the imaging environment to be uncoupled from the procedural environment so that expensive and often unavailable imaging equipment, such as stereotactic imaging equipment, need not be used.

More particularly, in one aspect of the invention a medical device is provided comprising a tube having a distal end, a proximal end, and a longitudinal axis, wherein the device is adapted for placement of the distal end thereof into a patient's body at a desired location. The medical device includes a fixation agent, which may comprise any one of a bonding agent, a mechanical fixation agent, or an electrosurgical coagulation element, disposed on the distal end thereof, which is adapted for affixing the distal end of the medical device at the desired location.

The medical device may comprise for example, a localization wire for use in connection with an open biopsy procedure. Alternatively, the device may comprise a tissue acquisition instrument, such as a biopsy instrument. In the preferred embodiment, the fixation agent is a bonding agent, comprising a surgical adhesive, glue, or solvent.

In another aspect of the invention, a tissue acquisition instrument is provided for retrieving body tissue, having a longitudinal axis and which comprises a distal end adapted for entry into a patient's body, a cutting element disposed on the instrument for cutting surrounding tissue, and structure disposed on the distal end for securing the tissue acquisition instrument at a predetermined desired location, in order to ensure that the tissue acquisition instrument remains in place during a tissue acquisition procedure so that desired tissue is properly acquired.

In yet another aspect of the invention, a method of performing a medical procedure is provided, using a medical device comprising a tube having a distal end, a proximal end, and a longitudinal axis. The method first comprises the step of placing the distal end of the tube in a patient's body, so that the distal end is disposed in a desired tissue location. Then, a bonding agent is dispensed for the tube into tissue surrounding the distal end, so that the distal end of the tube becomes affixed to the desired tissue location.

In still another aspect of the invention, a method is provided for performing a tissue acquisition procedure using a tissue acquisition instrument having a distal end, a proximal end a longitudinal axis, and a cutting element. In this method, the distal end of the instrument is placed into a patient's body, so that the distal end is disposed in a desired tissue location. Then, the distal end of the instrument is affixed to the desired tissue location, so that the instrument does not move relative to the desired tissue location during the tissue acquisition procedure. The-cutting element is then actuated to acquire one or more tissue samples.

The invention, together with additional features and advantages thereof, may best be understood by reference to the following description taken in conjunction with the accompanying illustrative drawing.

BRIEF DESCRIPTION OF THE DRAWING

FIG. 1 is a schematic plan view of a first embodiment of the present invention, illustrating a catheter for a localization wire introduction and infusion system wherein an introducer needle for introducing the localization wire into a patient's body remains in place during securement of the localization wire to surrounding tissue using a bonding agent;

FIG. 2 is a schematic plan view of the introducer needle used in conjunction with the catheter of FIG. 1;

FIG. 3 is a schematic plan view of one embodiment of a localization wire which may be used in conjunction with the infusion system shown in FIGS. 1 and 2;

FIG. 3a is a perspective view of the distal end of the embodiment shown in FIGS. 1-3, wherein the introducer needle is inserted through the lumen of the catheter;

FIG. 3b is a perspective view of the distal end of the embodiment shown in FIGS. 1-3, wherein the introducer needle is inserted through the lumen of the catheter, and its position within the catheter lumen is shown in phantom for illustrative purposes;

FIG. 3c is a perspective view similar to FIG. 3a, wherein the localization wire is inserted through the lumen of the catheter;

FIG. 4 is a perspective view of a second embodiment of the present invention, illustrating a second embodiment of a localization wire introduction and infusion system, wherein an introducer needle for introducing the localization wire into a patient's body is removed during securement of the localization wire to surrounding tissue using a bonding agent;

FIG. 5 is schematic plan view of the catheter for the system illustrated in FIG. 4;

FIG. 6 is a schematic plan view of the introducer needle for the system illustrated in FIGS. 4 and 5;

FIG. 6a is a perspective view of the distal end of the embodiment shown in FIGS. 4-6, wherein the localization wire is inserted through a lumen of the catheter;

FIG. 7 is a schematic plan view of a second embodiment of a localization wire which may be utilized in conjunction with either of the embodiments of FIGS. 1-3 or 4-6;

FIG. 8 is a schematic view in isolation illustrating one embodiment of the present invention for storing and releasing a bonding agent which is dispensed from a medical instrument for affixing the medical instrument to surrounding tissue in a patient's body;

FIG. 11 is a perspective view of a modified version of the embodiment shown in FIGS. 9 and 10, wherein the cannula is comprised of a braided polymer tubing and the interstices between the braids function as the infusion openings for infusing bonding agent to surrounding tissue;

FIG. 12 is a perspective view of another modified version of the embodiment shown in FIGS. 9 and 10, wherein the cannula is comprised of a coil and the interstices between expanded coils function as the infusion openings for infusing bonding agent to surrounding tissue;

DETAILED DESCRIPTION OF THE INVENTION

Figure 9:
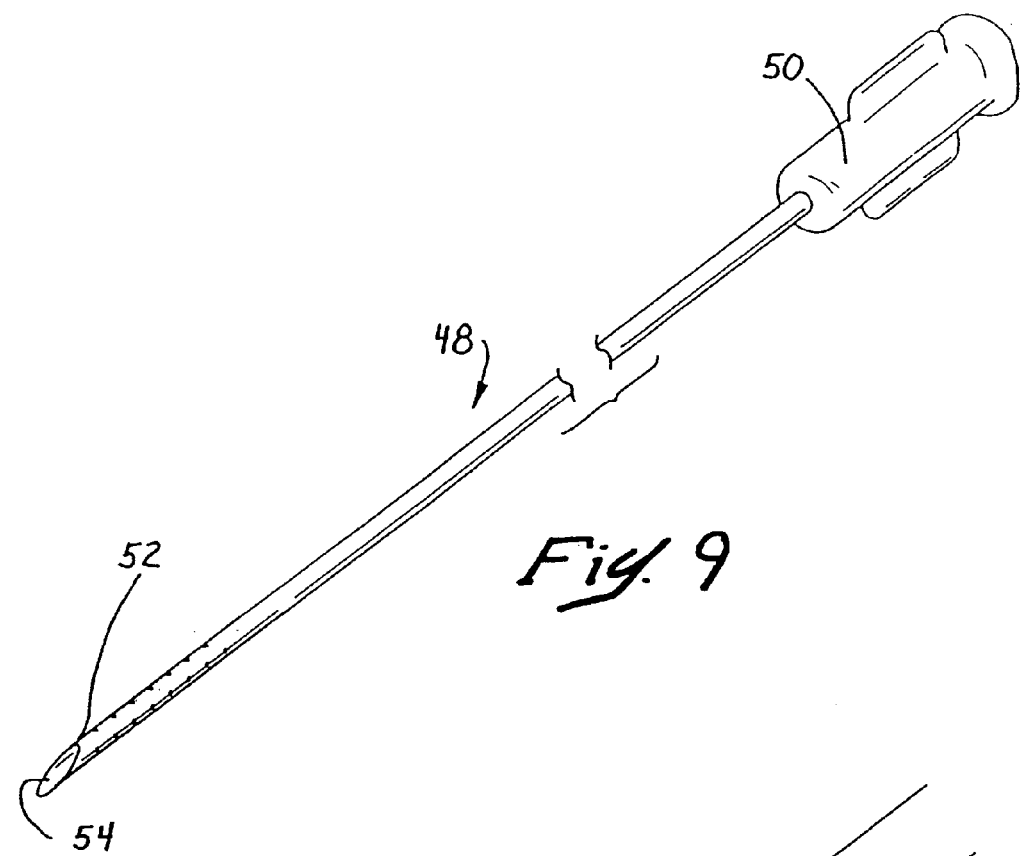
FIG. 9 is a perspective view of a third embodiment of the present invention, illustrating a catheter which may be used as a localization wire and infusion system.

Referring now more particularly to the drawings, FIGS. 1-3c illustrate a first embodiment of the invention, wherein a medical instrument 10 (FIGS. 3a-3c) comprises a catheter 12 (FIGS. 1, 3a-3c), an introducer needle 14 (FIGS. 2, 3a, and 3b), and a localization wire 16 (FIGS. 3, 3c). In this embodiment, which may be styled as a "needle in" infusion system, the introducer needle 14 comprises a sharp distal end 18, which is inserted through an entry hole 20 in the catheter 12 (FIG. 1), so that its tip 18 extends beyond the distal end 22 of the catheter 12, as shown in FIGS. 3a and 3b. The introducer needle 14 may include a stop 24 having an enlarged diameter, which is adapted to engage the distally tapering inner sidewall of the catheter 12 at a predetermined point, as generally shown particularly in FIG. 3b, to ensure that the tip 18 properly extends beyond the distal end 22 of the catheter 12. The introducer needle 14 and catheter 12 together are then introduced into a patient's body (not shown), using known imaging techniques for guiding localization wires to the site of tissue to be excised ("target tissue").

Once the catheter 12 and introducer needle 14 are in position relative to the target tissue, the introducer needle 14 is removed proximally from the catheter 12, and the localization wire 16 is inserted distally through the entry hole 20 and pushed distally through the lumen in the catheter 12, so that the distal end of the localization wire 16 extends distally of the distal end of the introducer needle and catheter, as shown in FIG. 3b. Indicator marks 25 preferably assist the practitioner in ensuring that the localization wire is properly inserted to the required depth.

Localization wires such as the wire 16 typically include some type of mechanical anchoring means, such as a barb or hook 26, for securing the distal end of the localization wire 16 in position behind the target tissue. However, this approach is often inadequate, as discussed supra in the Background portion of the specification, because the tissue to which the hook 26 becomes attached will often shift relative to the target tissue between the imaging step of the medical procedure, which is usually a biopsy, such as a breast biopsy, and the ensuing surgical step, which usually takes place in a different area of the hospital and requires transportation and resultant jostling of the patient from the radiology department to the operating room. The present invention, therefore, contemplates an advantageous additional step of employing a bonding agent, which may comprise any known material which is capable of creating a bond between the distal end of the medical instrument 10 and surrounding tissue. Once the localization wire is properly placed at the desired target tissue site, under imaging guidance, the bonding agent is dispensed from the distal end of the medical instrument to the surrounding tissue to create the desired bond. In the embodiment of FIGS. 1-3a, a plurality of infusion ports 28 are disposed along the length of the distal end of the catheter 12. Any number of infusion ports (one or more) may be employed in order to optimize the flow of bonding agent to the tissue, and they are preferably staggered circumferentially about the catheter in order to evenly deliver bonding agent about the circumference of the instrument 10. Various delivery means may be employed as well. For example, in the illustrated embodiment, the catheter 12 comprises a proximal hub 30 (FIG. 1), including a stopcock 32 which is engageable with a syringe (not shown) containing the bonding agent. When the localization wire is properly positioned, the practitioner injects the bonding agent into the lumen (not shown) of the catheter using the syringe with sufficient pressure that it flows distally through the lumen and is infused into surrounding body tissue through the infusion ports 28. The resultant bonding of the distal end of the localization wire 16 to the surrounding target tissue ensures with much greater certainty than the use of mechanical attachment means alone, such as the hook 26, that the localization wire will be properly positioned when the surgical procedure commences, thereby improving the likelihood that the proper target tissue will be excised with a minimum incision and resultant trauma to the patient.

Preferred bonding agents include any known effective biocompatible bonding materials, such as surgical adhesives, including cyanoacrylate, fibrin glue, and solvents.

An alternative to injection of the bonding agent through the lumen of the medical instrument 10 is illustrated in FIG. 8. The bonding agent 33 may be stored in a rupturable container 34 which is disposed in the distal end of the medical instrument 10, adjacent to the infusion ports 28. When it is desired to release the bonding agent 33 through the infusion ports, a puncturing device 36 may be actuated by the practitioner to rupture the container 34. In the illustrated embodiment, the device 36 comprises a simple "spear" which is actuated distally to rupture the container, but it may alternatively comprise any suitable configuration for functioning equivalently. Additionally, it is within the scope of the invention to employ a chamber for containing the bonding agent which includes a valved port, wherein the valve is actuated to an open position by the practitioner to release the bonding agent. Various other embodiments for accomplishing this function, as would be known to one of ordinary skill in the art, are deemed to fall within the scope of the invention as well.

Once the localization wire is securely bonded to the surrounding tissue, the practitioner may withdraw the catheter and introducer needle assembly, leaving the localization wire in place to mark the target tissue for the ensuing surgical step in the biopsy or other medical procedure.

FIGS. 4-7 illustrate a second "localization wire" embodiment, wherein like elements to those shown in the first embodiment are designated by like reference numerals, succeeded by the letter "a". This system may be styled as a "needle out" infusion system. In this embodiment, the catheter 12a comprises a dual lumen extrusion, including first and second lumens 38 and 40, respectively (FIG. 6a). The first lumen 38 accommodates the bonding agent, while the second lumen accommodates the localization wire. The catheter 12a further includes a dual lumen proximal hub 42, which comprises a localization wire entry port 44 and a stopcock 32a.

In operation, the introducer needle 14 a is disposed coaxially outside of the catheter 12a, as illustrated in FIG. 4, and the instrument 10a is inserted into the patient's body in known fashion, under conventional imaging guidance. The localization wire 16a is inserted distally through the port 44, either before or after introduction of the instrument 10a into the patient's body. As in the first embodiment, once the instrument 10a is placed, the localization wire 16a is advanced distally until the indicator marks 25a indicate to the practitioner that the distal hook 26a is distal of the distal end of the catheter 12a and of the target lesion, as shown by the imaging equipment. The localization wires of FIGS. 3 and 7 may be used interchangeably in either of the two disclosed embodiments, and are substantially identical except that the localization wire 16a includes filaments 46 near its distal end which provide additional surface area for bonding.

As in the previous embodiment, once the localization wire is in the proper position, bonding agent is injected into the catheter 12a, preferably using a syringe which is engaged with the stopcock 32a, so that the bonding agent flows distally through the first lumen 38 and is infused through the infusion ports 28a. Again, the infusion ports may be disposed about the catheter, in rows offset by 90 degrees with respect to one another, or otherwise staggered so that the bonding agent is evenly disposed about the catheter. Alternatively, as in the previous embodiment, the bonding agent may be stored in the distal end of the instrument 10a using an apparatus like that illustrated in FIG. 8. It is within the scope of this invention, as well, to store or inject two or more bonding agent compounds, comprising a reactant and a catalyst, at the injection site, and to mix the reactant and catalyst together at the appropriate time to catalyze a bonding agent.

Once the bonding agent has been injected, but before it has solidified, the catheter 12a and introducer needle 14a are withdrawn from the patient's body, leaving the localization wire in place.

Figure 10:
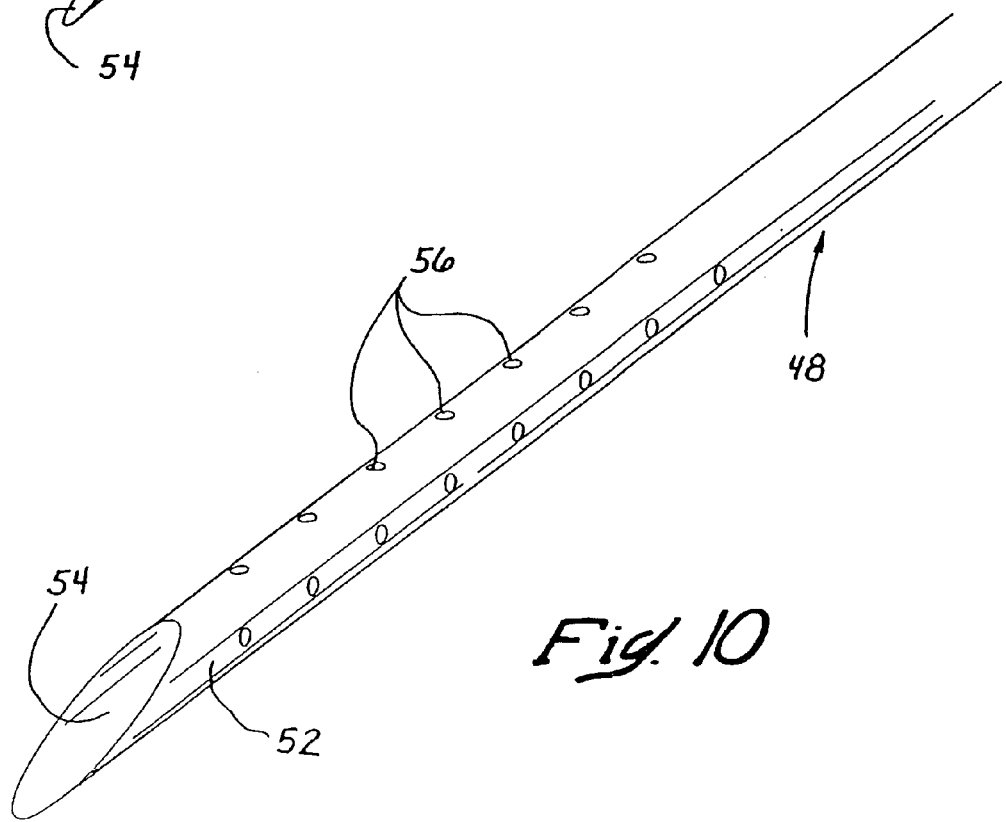
FIG. 10 is an enlarged perspective view of the distal end of the cannula illustrated in FIG. 9, showing in greater detail the perforations in the distal end for infusing a bonding agent to surrounding tissue.

Still a third embodiment, which functions in a manner equivalent to that of a localization wire, is illustrated in FIGS. 9 and 10. In this embodiment, a catheter 48, which comprises a proximal hub 50, a distal end 52, and a lumen 54, is insertable into a patient's body using conventional image guidance techniques, so that the distal end 52 is disposed at a desired target tissue site. Once properly located, a bonding agent 33 is infused through one or more infusion ports 56 to surrounding target tissue, in order to bond the distal end of the catheter 48 to the surrounding tissue. Again, as in the previous embodiments, the bonding agent may be injected into the lumen 54 of the catheter through the proximal hub 50, or may alternatively be stored in the distal end 52 of the catheter and selectively released at the desired time.

FIGS. 11 and 12 illustrate two alternative embodiments for the outer tube 58 of the catheter in any of the foregoing embodiments. In FIG. 11, the tube 58 comprises a stainless steel braid, the proximal end 60 of which is encapsulated by a polymer, such as polyamide, and the distal end 62 of which is exposed. The exposed distal end is preferably approximately 1-2 centimeter (cm) in length, though it may be longer or shorter if desired. In operation, interstices 64 between bands 66 of the exposed braided portion 62 function as openings for permitting infusion of bonding agent to surrounding tissue, instead of the infusion ports disclosed in the preceding embodiments. If the exposed braided portion is expanded, the interstices will be enlarged and will permit the flow of more bonding agent therethrough.

In a manner in some respects similar to the embodiment of FIG. 11, the FIG. 12 embodiment comprises an outer tube 58 having a sleeve 68 surrounding a coil 70 of suitable material. In the distal end of the tube 58, the coil 70 may be stretched to create interstices 72 between bands 74 of the coil. Bonding material may be infused, as desired, outwardly through the interstices 72 of the expanded coil, and then through holes 76 in the sleeve 68 to surrounding tissue. Alternatively, the sleeve could be retracted to expose the coil, in which case the sleeve holes 76 would be unnecessary.

Figure 13:
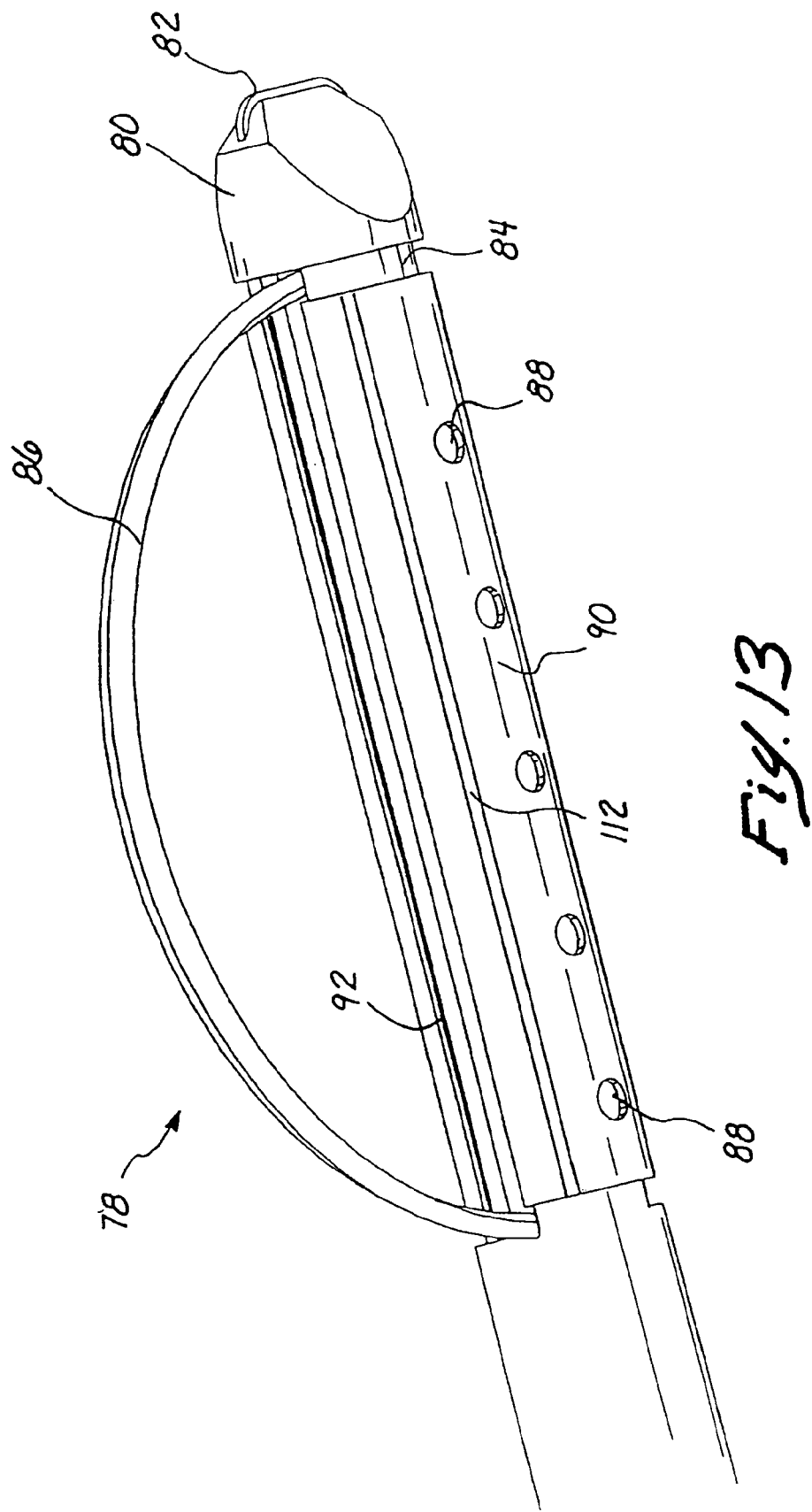
FIG. 13 is a perspective view of a biopsy instrument constructed in accordance with the principles of the present invention.

FIG. 13 illustrates the distal end of a medical instrument 78 which is shown and described in co-pending application Ser. No. 09/057,303, commonly assigned with the present application and expressly incorporated by reference herein. The instrument 78 comprises a tissue acquisition or biopsy instrument and preferably includes a tip 80 having an electrosurgical element 82 for entering tissue, and a shaft 84, on which is disposed a radially extendable and retractable cutting element or wire 86. The cutting element 86 is preferably energized by RF energy provided by an electrosurgical generator.

In operation, the instrument 78 is moved axially to a position wherein the distal tip 80 is preferably distal to a target lesion or tissue to be removed, using a suitable imaging technique. In the prior art, such imaging techniques for biopsy procedures and the like typically include the use of a stereotactic or sonographic imaging system, both of which are relatively expensive and not always available in an average community hospital. This approach is designed to combine the imaging and cutting steps so that both occur simultaneously. For example, in the case of a breast biopsy procedure, the breast is clamped in order to effectively utilize the imaging equipment, after which the instrument is inserted into the breast under imaging guidance to the lesion location. Then, under continued imaging guidance, the cutting element is actuated and the target tissue removed.

However, an important advantage of the present invention is the ability to "uncouple" the imaging environment from the procedural environment in a typical surgical or biopsy procedure, and the resultant important ability to utilize unmodified mammography equipment, readily available in most hospitals, to position the distal end of the instrument during the imaging step, rather than expensive and specialized stereotactic equipment. Then, the procedural step may occur later, in another area of the hospital. In the case of breast biopsies, this "uncoupling" also permits the patient's breast to be unclamped for the procedural step, resulting in increased patient comfort and easier working conditions for the practitioner.

These advantages are made possible because the inventive apparatus and technique permits the securement of the distal end of the instrument to the target tissue or lesion with sufficient confidence that the patient may be moved to the procedural environment without fear of having it slip away from the target tissue. This securement is accomplished using a fixation agent, which preferably comprises a bonding agent like that disclosed in connection with the foregoing localization wire and catheter embodiments. In a manner similar to those embodiments, once the instrument is positioned in a desired position, the bonding agent is injected into a lumen of the instrument, or, alternatively, in a manner like that described supra, released from a container or chamber in the distal end of the instrument, so that it may be infused from one or more infusion ports 88 disposed on the distal end of the instrument. Preferably, the ports 88 are disposed on a bushing or sleeve 90 which has a linear slot 92 for permitting passage of the cutting element 86 as it is extended and retracted radially, and which is rotatable relative to the shaft 84. Thus, when the bonding agent is infused to the surrounding tissue, so that the bushing 90 is affixed in place relative to the surrounding tissue, the cutting element 86 will still be rotatable on the underlying shaft 84 in order to permit circumferential cutting of tissue, as desired, during the later procedural step. Suitable care is taken that only a sufficient amount of bonding agent is dispensed to bond the bushing to surrounding tissue, and not the shaft or tip of the instrument, in order that the shaft and tip continue to be rotatable relative to the bushing.

Of course, the bushing 90 may be constructed in number of alternative ways, as will be apparent to those of ordinary skill in the art. For example, as shown in FIGS. 11 and 12, the bushing could be comprised of a braided or coil material, so that interstices between braids or coils thereof could function as the infusion openings.

Figure 14:
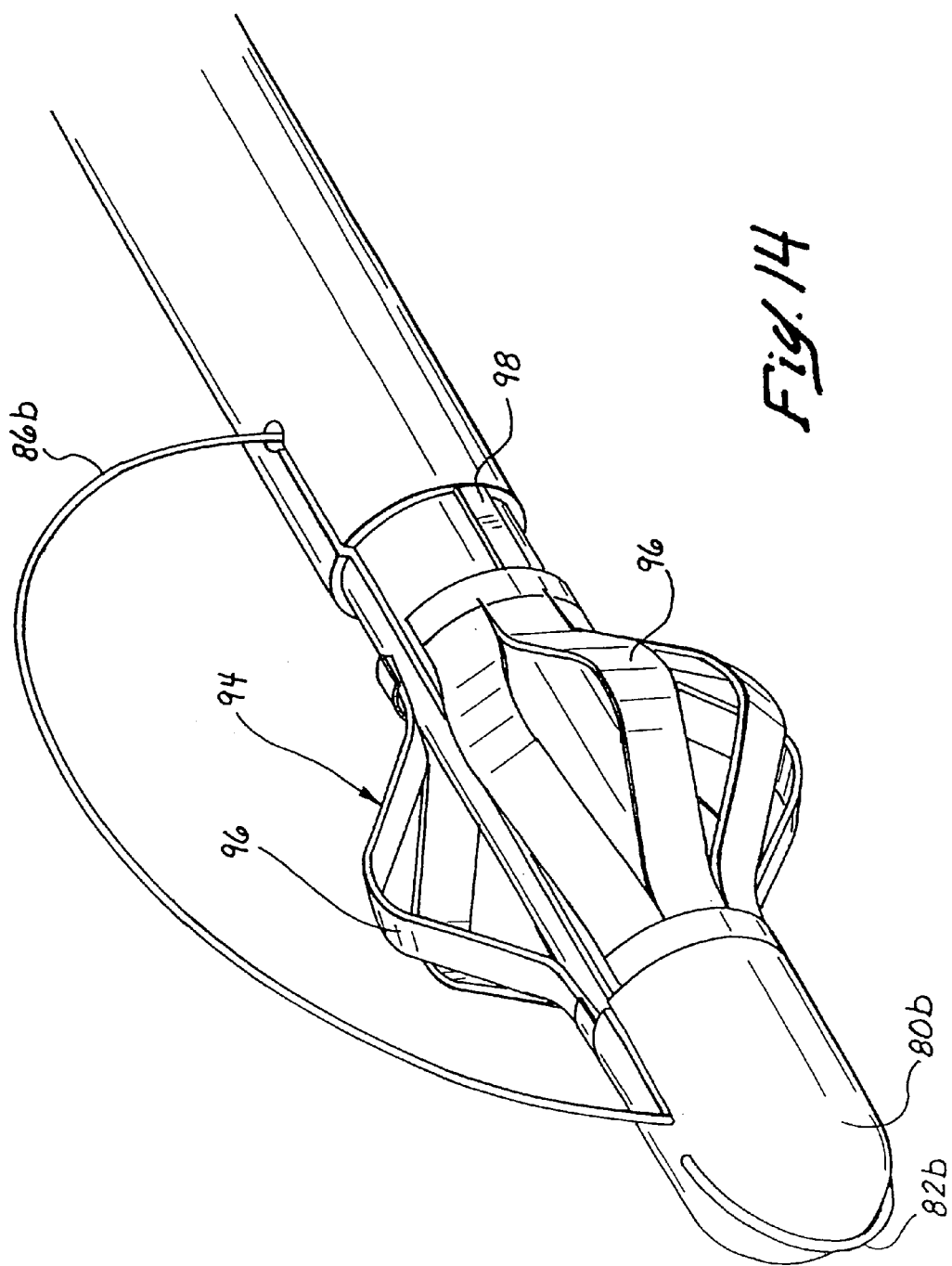
FIG. 14 is a perspective view of a second modified embodiment of a biopsy instrument having an expandable Mallicot structure at its distal end for anchoring the instrument at a particular tissue site.

Rather than using a bonding agent, a mechanical fixation agent may be utilized to secure the distal end of the instrument to surrounding tissue. For example, FIG. 14 illustrates an alternative embodiment to that of FIG. 13, wherein a mechanical fixation structure 94 is utilized to secure the distal end of the instrument to surrounding tissue, rather than a bonding agent. In this embodiment, wherein like elements to those of FIG. 13 are designated by like reference numerals, succeeded by the letter "b", the mechanical fixation structure 94 comprises an expandable Mallicot structure, having a rotatable bushing 90b and a plurality of expandable bands 96. Actuating pushrods 98, of which there are preferably four, arranged circumferentially 90 degrees apart, are provided to actuate the bands 96 between their expanded positions (as shown), in which they are positioned to anchor the distal tip 80b to the desired tissue site, and their retracted positions.

Figure 15:
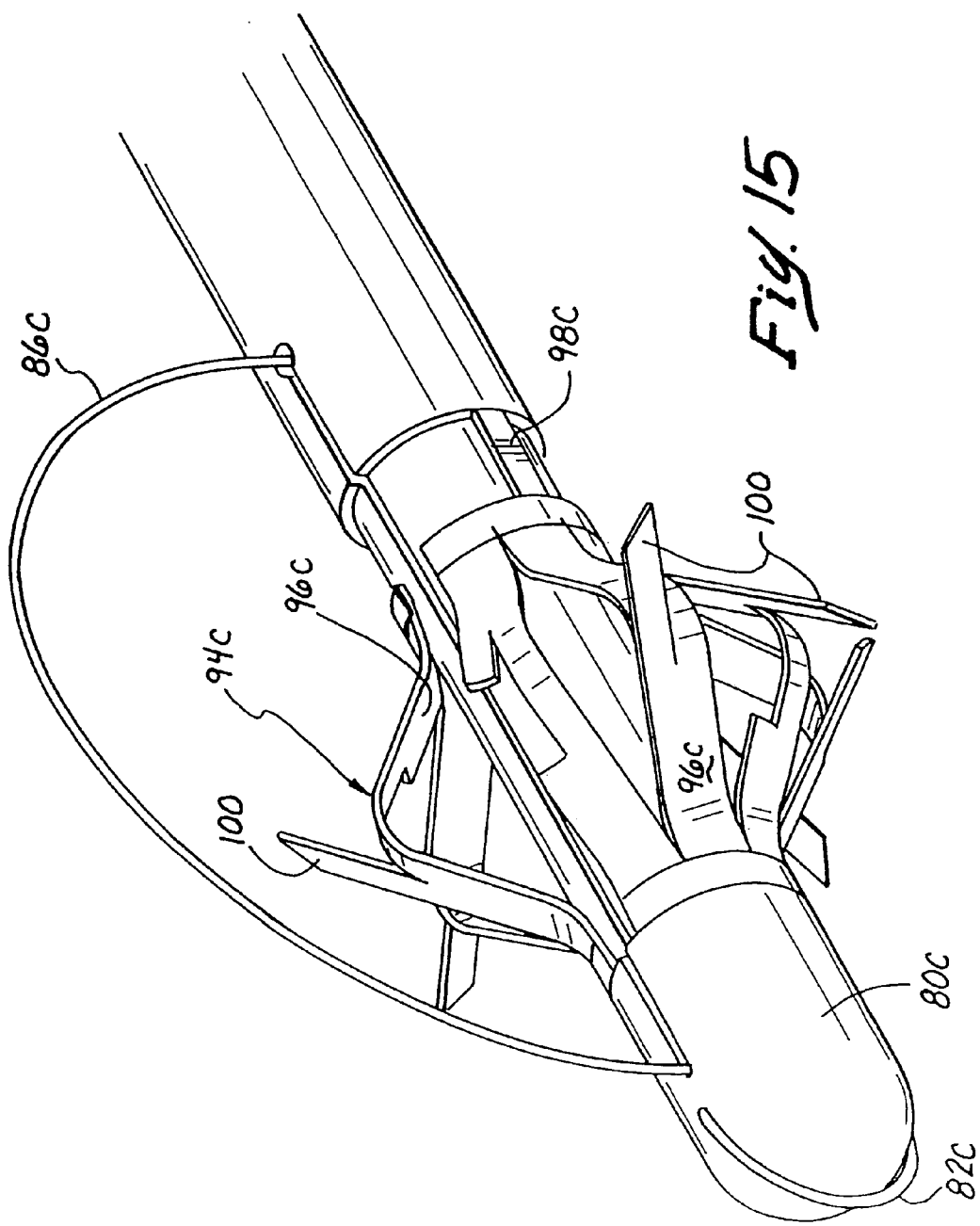
FIG. 15 is a perspective view of a third modified embodiment of a biopsy instrument having a modified expandable Mallicot structure at its distal end for anchoring the instrument at a particular tissue site.

FIG. 15 illustrates another modified embodiment which is similar to that of FIG. 14, and wherein like elements to those of FIG. 14 are designated by like reference numerals, succeeded by the letter "c". The only difference between this embodiment and the FIG. 14 embodiment is that the bands 96c are split at their centers, to form protruding portions 100, for the purpose of permitting further radial extension of each band and to also permit the protruding portions 100 to attach themselves to adjacent tissue.

Figure 16:
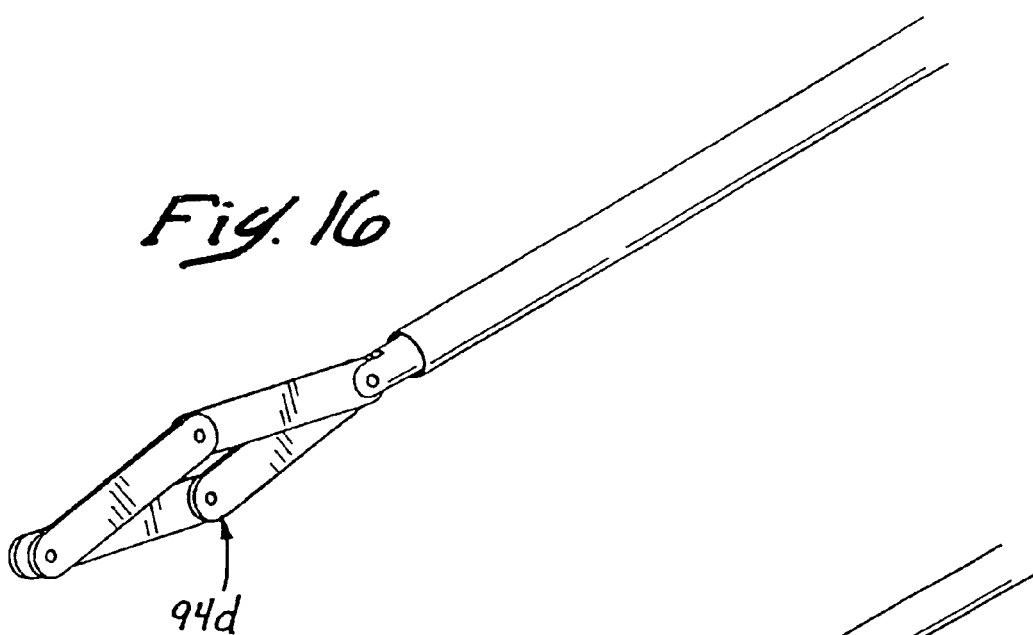
FIG. 16 is a perspective view of a fourth modified embodiment of a biopsy instrument having an expandable linkage structure at its distal end for anchoring the instrument at a particular tissue site, wherein the linkage structure is shown in its retracted position.
Figure 17:
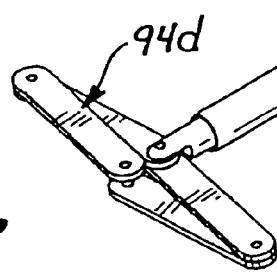
FIG. 17 is a perspective view of the embodiment shown in FIG. 16, wherein the linkage structure is shown in its expanded position.

FIGS. 16 and 17 schematically illustrate still another modified mechanical fixation structure 94d, comprising a linkage, which may be substituted for the structures 94 and 94c of FIGS. 14 and 15, respectively, wherein FIG. 16 illustrates the linkage in its retracted configuration and FIG. 17 illustrates it in its radially expanded configuration.

Figure 18:
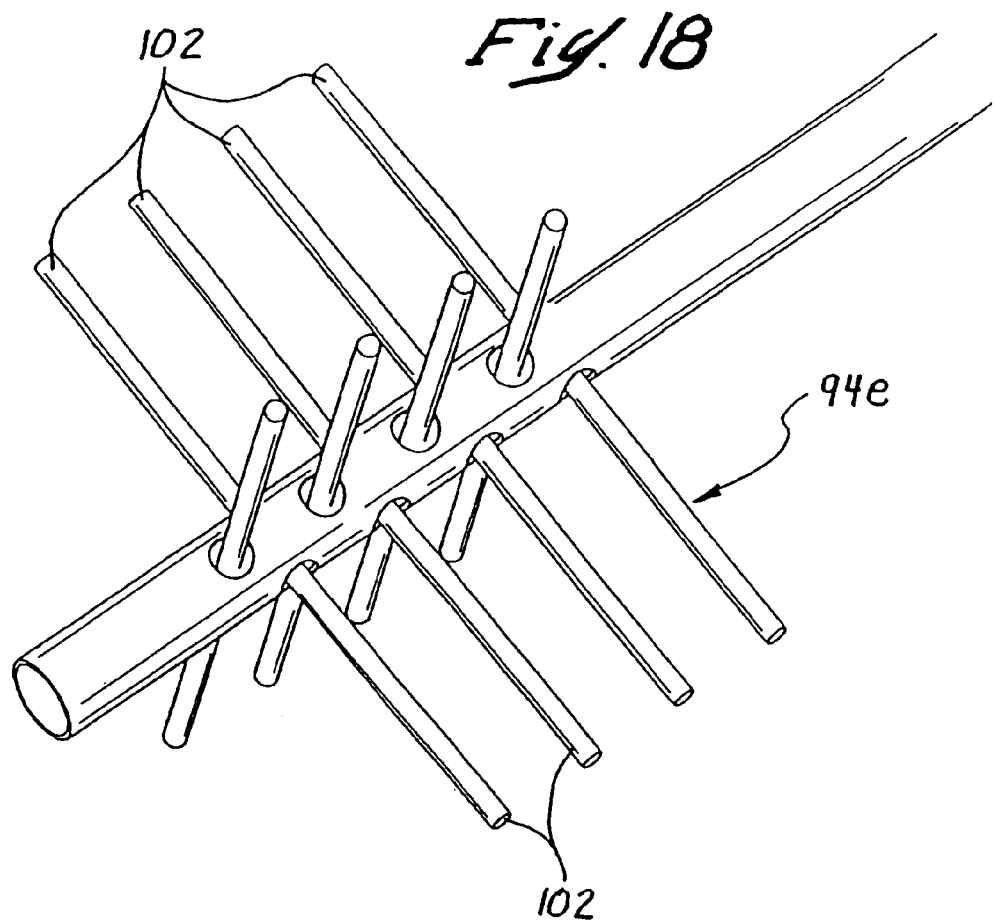
FIG. 18 is a perspective view of a fourth modified embodiment of a biopsy instrument having an extendable "bottle brush" structure at its distal end for anchoring the instrument at a particular tissue site.

FIG. 18 schematically illustrates yet another modified mechanical fixation structure 94e, comprised of a plurality of radially retractable and extendable wires 102.

Figure 19:
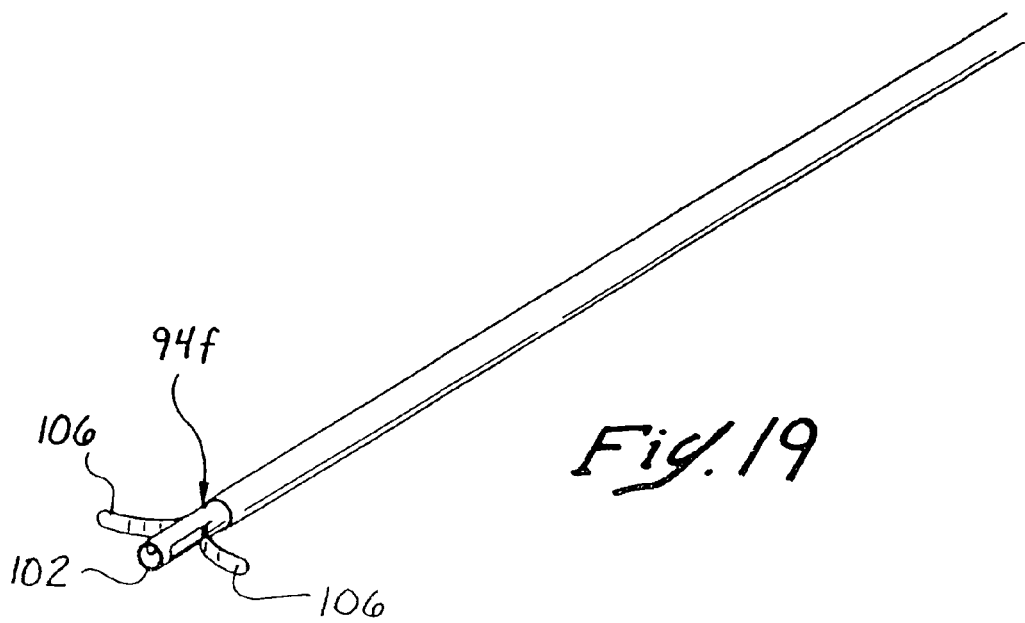
FIG. 19 is a perspective view of a fifth modified embodiment of a biopsy instrument having a nitinol flap structure at its distal end, expandable upon retraction of a surrounding sleeve, for anchoring the instrument at a particular tissue site.

FIG. 19 schematically illustrates still another modified mechanical fixation structure 94f, of the bone anchor type, comprised of a nitinol tube 104 and radially expandable flaps 106.

Figure 20:
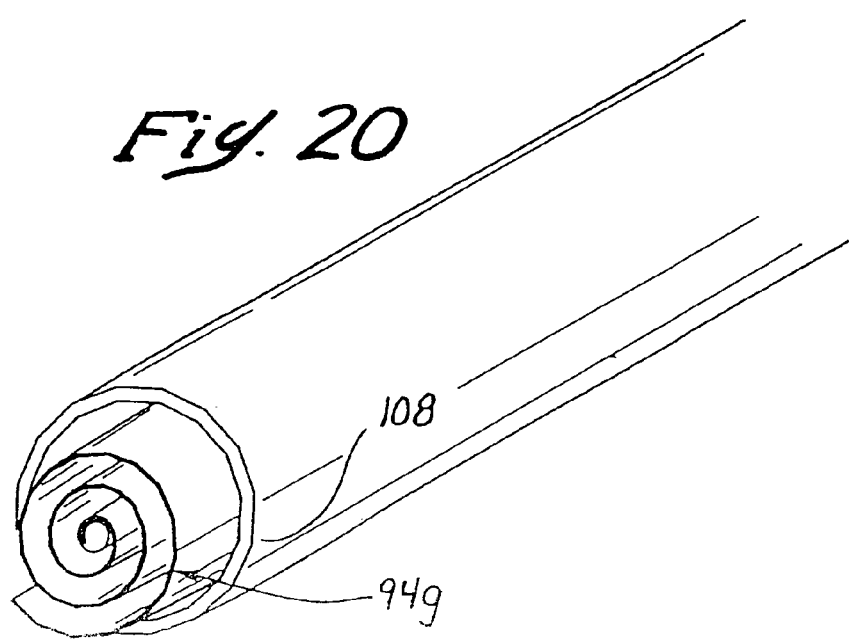
FIG. 20 is a perspective view of a sixth modified embodiment of a biopsy instrument having a rolled stent structure at its distal end which unrolls upon retraction of a surrounding sleeve, for anchoring the instrument at a particular tissue site.

In FIG. 20, there is shown another modified mechanical fixation structure 94g, comprised of a rolled stent which may be unrolled to expand radially and provide an anchoring function by axially retracting a sleeve 108.

Figure 21:
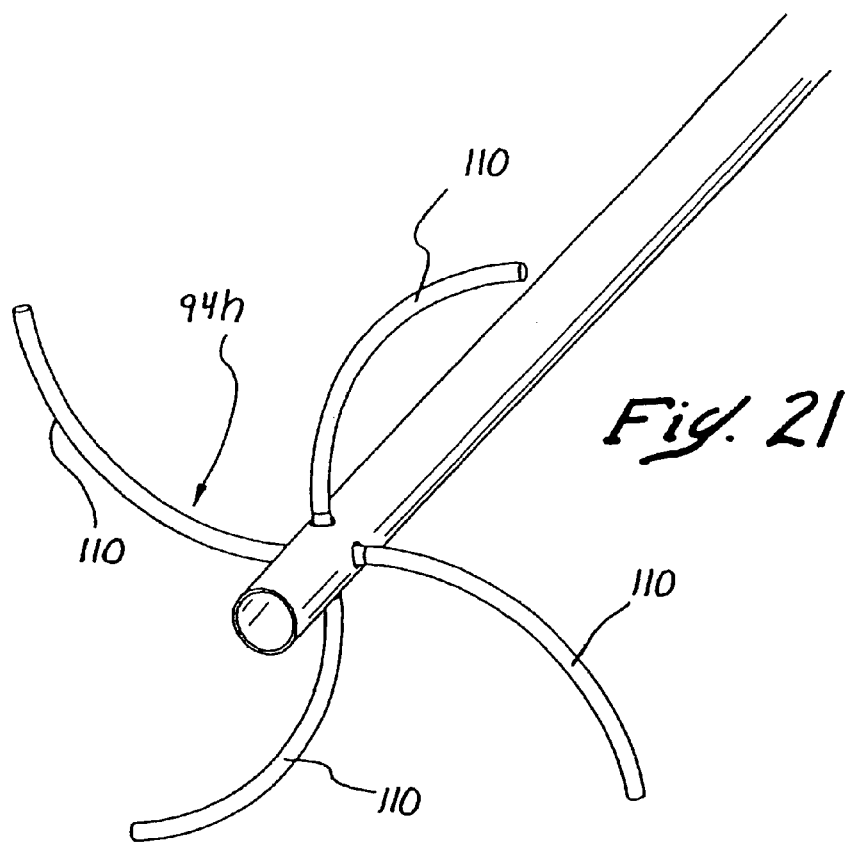
FIG. 21 is a perspective view of a seventh modified embodiment of a biopsy instrument having expandable spiral wires at its distal end for anchoring the instrument at a particular tissue site.

FIG. 21 shows still another modified mechanical fixation structure 94h comprised of a plurality of extendable wires 110.

Figure 22:
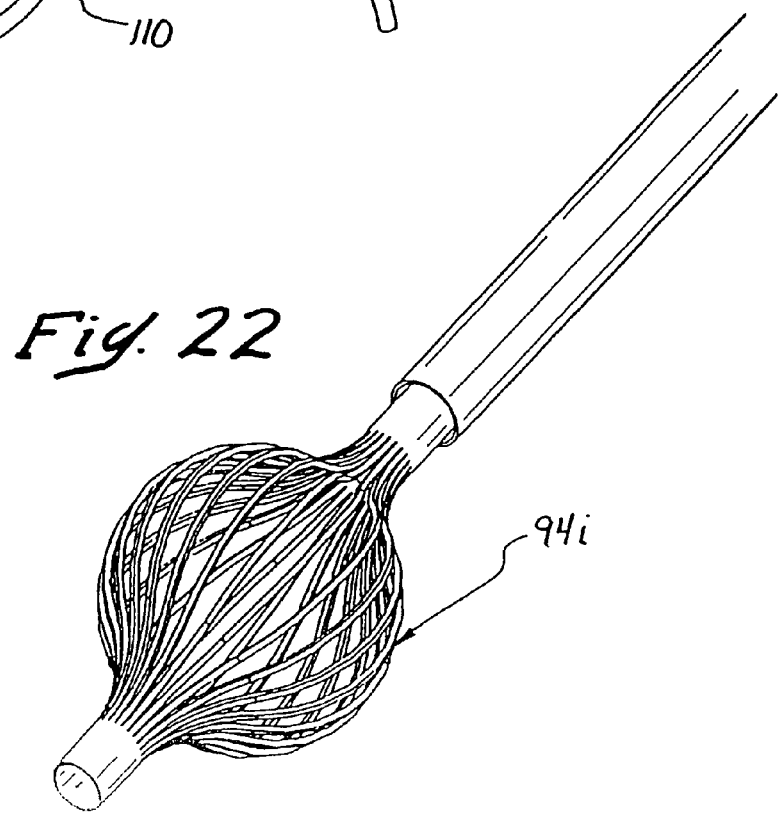
FIG. 22 is a perspective view of an eighth modified embodiment of a biopsy instrument having an expandable basket at its distal end for anchoring the instrument at a particular tissue site.

FIG. 22 illustrates a modified mechanical fixation structure 94i which comprises a radially expandable and retractable basket.

Any of the foregoing mechanical fixation structures may be interchangeably employed in the embodiments of FIGS. 14 and 15, and it is within the scope of this invention to also employ other mechanical fixation structures which are known conventionally for anchoring medical devices in the body.

Still another means for bonding the distal end of the instrument 78 to surrounding tissue, which is within the scope of the present invention, is to apply RF energy to the tissue, using an electrosurgical coagulation element. The electrosurgical coagulation element may comprise one of the existing electrosurgical elements 82 or 86, or preferably another coagulation element 112 (FIG. 13) which may be disposed on or near the bushing 90. Activation of the coagulation element 112 for a short interval coagulates the tissue-surrounding the tissue, thereby bonding the bushing to the tissue. Alternatively, the element 112 could comprise a heating rod for cauterizing tissue, similar to the function of a branding iron, to produce the same type of bonding effect by "sticking" the cauterized tissue to the distal end of the instrument.

This approach may also be utilized in the localization wire embodiments illustrated in FIGS. 1-12, by employing an electrosurgical coagulation element on the distal end thereof, which is connected to a suitable electrosurgical generator, or, alternatively, by employing an electrical heating element for cauterizing tissue.

While this invention has been described with respect to various specific examples and embodiments, it is to be understood that the invention is not limited thereto and that it can be variously practiced within the scope of the following claims.

What is claimed is:

1. A method for performing a tissue acquisition procedure comprising:
   a) providing a tissue acquisition instrument having a distal end, a proximal end, a longitudinal axis, a tissue cutting element along a length of a distal portion proximal to the distal end, and at least one radially extendable and retractable member with a free end within said length, the method comprising:
   b) placing the distal end of the instrument in a patient's body, so that the length of the distal portion proximal to the distal end is disposed in a desired tissue location; and
   c) affixing the length of the distal portion of the instrument to said desired tissue location by extending the at least one radially extendable and retractable member into surrounding tissue radially and oriented in a proximal or distal direction, so that the free end of the at least one radially extendable and retractable member engages tissue at the desired tissue location so that the distal end of the instrument does not move axially relative to the desired tissue location during the tissue acquisition procedure.

2. A method for performing a tissue acquisition procedure at an intracorporeal site within a patient comprising:
   a) providing a tissue acquisition instrument having a longitudinal axis, a distal end, a distal shaft portion proximal to the distal end, an elongated tissue cutting element on the distal shaft portion extending along a length thereof and a plurality of fixation elements on the distal shaft portion within the length thereof;
   b) advancing the tissue acquisition instrument within the patient until the distal shaft portion of the instrument is at the desired intracorporeal site within the patient;
   c) affixing the distal portion of the tissue acquisition instrument at the intracorporeal site by expanding at least one of the fixation elements radially away from the longitudinal axis in a proximal direction from the distal shaft portion and by expanding at least one of the fixation elements away from the longitudinal axis in a distal direction from the distal shaft portion, so that the instrument does not move along its longitudinal axis relative to the site during tissue acquisition; and
   d) rotating the elongated cutting element about the distal shaft portion of the instrument to cut tissue to be acquired from supporting tissue at the intracorporeal site.

3. The method of claim 2, wherein the tissue acquisition instrument has a plurality of radially extendable and retractable first and second fixation elements.

4. The method of claim 2, wherein the tissue acquisition instrument has a radially expandable tissue cutting element proximal to the distal end.

5. The method of claim 2, wherein the distal tip of the tissue acquisition instrument is advanced through the patient's body until the distal tip thereof is disposed adjacent and distal to the desired intracorporeal site.

6. The method of claim 2, wherein the tissue acquisition instrument has a distal tissue penetrating tip to facilitate advancement through tissue to the tissue site.

7. The method of claim 6, wherein the distal penetrating tip has a tissue cutting element.

8. The method of claim 7, wherein the tissue cutting element on the distal tip of the tissue acquisition instrument is an electrosurgical cutting element.

9. A method for performing a tissue acquisition procedure at an intracorporeal site within a patient comprising
   a) providing a tissue acquisition instrument having an elongated shaft with a longitudinal axis, a distal end with a distal tip, a proximal end, a distal shaft portion proximal to the distal end, an elongated tissue cutting element on the distal shaft portion extending along a length thereof and a plurality of fixation elements on the distal shaft portion within the length thereof with a first fixation element which extends away from the distal shaft portion in the proximal direction, which has a free end configured to engage target tissue, which has another end secured to the distal shaft portion at a location spaced proximally from the distal tip and which has a radially retracted configuration for delivery and a radially extended configuration for deploying the free end into tissue at the target site and with a second fixation element which extends away from the distal shaft portion in the distal direction, which has a free end configured to engage target tissue, which has another end secured to the distal shaft portion at a location spaced proximally from the distal tip and which has a radially retracted configuration for delivery and a radially extended configuration for deploying the free end into tissue at the target site;
   b) advancing the tissue acquisition instrument within the patient until the distal portion of the instrument is at the desired intracorporeal site within the patient;
   c) affixing the distal portion of the tissue acquisition instrument at the intracorporeal site by expanding at least one of the fixation elements radially away from the longitudinal axis in a proximal direction and by expanding at least one of the fixation elements away from the longitudinal axis in a distal direction, so that the instrument does not move along its longitudinal axis relative to the site during tissue acquisition; and
   d) rotating the elongated cutting element about the distal shaft portion of the instrument to cut tissue to be acquired from supporting tissue at the intracorporeal site.

10. The method of claim 9, wherein the radially expandable tissue cutting element is an electrosurgical cutting element.

11. The method of claim 9, wherein a plurality of fixation elements extend from a location on the distal shaft portion spaced proximal to the distal end into tissue at the target site.

12. A method of claim 11, wherein the first fixation element which extends away from the distal shaft portion in a proximal direction, which has a free end, which has another end secured to the distal shaft portion proximal of the distal tip and which is configured for securing the distal shaft portion of the medical device within tissue at the target site; and the second fixation element which extends away from the distal shaft portion in a distal direction, which has a free end, which has another end secured to the distal shaft portion proximal of the distal tip and which is configured for securing the distal shaft portion of the medical device within tissue at the target site.

13. The method of claim 12, wherein the free end of the fixation elements are configured for penetrating tissue at the target site.

14. The method of claim 13, wherein the fixation elements have a radially retracted configuration for delivery and a radially extended configuration for deploying the free end into tissue at the target site.

* * * * *